(12) United States Patent
Yoshida et al.

(10) Patent No.: US 6,641,827 B2
(45) Date of Patent: *Nov. 4, 2003

(54) INSECTICIDE OBTAINED FROM PLANTS FOR USE ON TERMITES

(75) Inventors: Shinji Yoshida, Osaka (JP); Akira Igarashi, Takarazuka (JP)

(73) Assignee: Takeda Chemical Industries, Ltd., Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/378,508

(22) Filed: Aug. 20, 1999

(65) Prior Publication Data

US 2003/0082244 A1 May 1, 2003

(30) Foreign Application Priority Data

Aug. 21, 1998 (JP) .............................. 10-235943

(51) Int. Cl.$^7$ ......................... A01N 25/00; A01N 65/00; A01N 35/78
(52) U.S. Cl. ........................................ 424/405; 424/725
(58) Field of Search ................................ 424/405, 93.7, 424/94.1, 195.1, DIG. 10, 725

(56) References Cited

U.S. PATENT DOCUMENTS

| | | | | |
|---|---|---|---|---|
| 5,591,435 A | * | 1/1997 | Vaccarello-Dunkel et al. | 424/195.1 |
| 5,703,052 A | * | 12/1997 | Deninno et al. | 514/26 |
| 6,063,381 A | * | 5/2000 | Staggs | 424/195.1 |

FOREIGN PATENT DOCUMENTS

| | | | |
|---|---|---|---|
| DE | 19530894 | * | 2/1997 |
| DE | 19530894 A1 | * | 2/1997 |
| JP | 29-4950 | | 8/1954 |
| JP | 41-16320 | | 9/1966 |
| JP | 77017099 B | * | 5/1977 |
| JP | 56077212 A | * | 6/1981 |
| JP | 2-131416 A | * | 5/1990 |
| JP | 3-41011 | | 2/1991 |
| JP | 4-247004 | | 9/1992 |
| JP | 5-255007 | | 10/1993 |
| JP | 6-329514 | | 11/1994 |
| JP | 10-130114 | | 5/1998 |

OTHER PUBLICATIONS

Carter et al. Termiticidal Components of Wood Extracts: 7–Methyljuglone from Diospyros v., J. Agric. Food Chem, Abstr. Only, 1978.*
Klocke et al., The Ellagitannin Geraniin and its Hyclolysis Products Isolated as Insect Growth Inhib . . . ,Phytoch. Abstr. Only, 1986.*
Khanna et al., New Sources of Insecticides & Pesticides; Int. Congr. Plant Tissue Cell Cult., Abstract Only, 1986.*
Agrow, Natural Sources for New Agrochem., See Abstr. Only, 1989.*
Carter et al., "Termiticidal Components of Wood Extracts: 7–Methyljuglone from Diospyros virginiana" J. Agric. Food Chem., Vol 26, No. 4, pp. 869–873, 1978.*

* cited by examiner

*Primary Examiner*—David M. Naff
*Assistant Examiner*—Deborah K. Ware
(74) *Attorney, Agent, or Firm*—Wenderoth, Lind & Ponack, L.L.P.

(57) ABSTRACT

An insecticide application to termites is obtained comprising at least one member selected from a plant, an extract of the plant, and an ooze (or exudate) of the plant, wherein the plant belongs to at least one genus selected from the group consisting of the genus Geranium, the genus Morus, the genus Artemisia, the genus Diospyros, the genus Crataegus, the genus Curcuma, the genus Rubia, the genus Polygonum, the genus Gardenia, the genus Cornus, the genus Uncaria, the genus Rheum, the genus Terminalia and the genus Saussurea. The extract may be a substance extracted with at least one member selected from the group consisting of water and a hydrophilic solvent. The insecticide exhibits high insecticidal and insect-controlling activity against insects (e.g., sanitarily injurious insects, insects injurious to houses and particularly to timber such as termites), being highly safe to human beings and animals and not adversely affecting the environment.

13 Claims, No Drawings

INSECTICIDE OBTAINED FROM PLANTS FOR USE ON TERMITES

FIELD OF THE INVENTION

The present invention relates to an insecticide useful for exterminating or controlling termites or other insects (e.g., injurious insects), a process for producing the same, and a method for exterminating or controlling insects (e.g., injurious insects) using the same.

BACKGROUND OF THE INVETNION

As insecticides or insecticidal compositions for exterminating or controlling termites, cockroaches and other injurious insects, there have been used highly insecticidal chemically synthesized agents. These agents are, however, highly harmful to human beings and animals and strongly affect the environment, having possibilities of destroying the ecosystem of nature.

Insecticides derived from natural materials have also been known. For example, obacunone in *Phellodendron amurense* Rupr., *P. molle* Nakai and berberine in the root of *Coptis japonica* Makino and the cortex of *Phellodendron amurense* Rupr. have been recognized to be effective in controlling or destroying termites.

As a highly safe agent for controlling or exterminating termites, Japanese Patent Application Laid-Open No. 41011/1991 (JP-A-3-41011) discloses an insecticide containing as an effective ingredient (or an active ingredient) an extract extracted with an organic solvent or a water-containing solvent from the neem tree. Moreover, Japanese Patent Application Laid-Open No. 329514/1994 (JP-A-6-329514) discloses the use of a component extracted or oozed from a plant of, e.g., the genus Moringa or the genus Marah as an insecticide or an agent for controlling or exterminating injurious insects. However, the effects of exterminating or controlling injurious insects of these plants have not reached a desired level yet.

SUMMARY OF THE INVENTION

Accordingly, an object of the present invention is to provide an insecticide or an agent for exterminating or controlling insects (e.g., injurious insects) of high insect-repellency and insecticidal activity, and a process for producing the same.

Another object of the present invention is to provide an insecticide or an insect-repellent agent which is highly safe to human beings and animals and does not adversely affect the environment, and a process for producing the same.

Another object of the present invention is to provide a method for exterminating or controlling insects (e.g., injurious insects) assuredly and efficiently.

The inventors of the present invention made extensive studies to obtain an insecticide or an insect-repellent agent which is derived from a plant and exhibits high insecticidal activity and repellency against insects, and found that components contained in specific plants, extracts or oozes thereof are highly safe, insecticidal and insect-repellent. The present invention is based on the above findings.

Thus, the insecticide or insect-repellent agent of the present invention comprises at least one member selected from a plant, an extract of the plant, and an ooze of the plant, each containing an insecticidal component, wherein the plant belongs to at least one genus selected from:

(1) the genus Geranium,
(2) the genus Morus,
(3) the genus Crataegus,
(4) the genus Rubia,
(5) the genus Artemisia,
(6) the genus Curcuma,
(7) the genus Gardenia,
(8) the genus Cornus,
(9) the genus Terminalia,
(10) the genus Saussurea,
(11) the genus Uncaria,
(12) the genus Rheum,
(13) the genus Diospyros, and
(14) the genus Polygonum.

The extract may be a substance extracted with at least one member selected from water and a hydrophilic solvent. The amount of the insecticidal component is 0.01 to 80% by weight relative to the insecticide in terms of the extract or ooze.

The present invention further includes a process for producing an insecticide or an insect-repellent agent which comprises subjecting a plant to at least one step selected from the group consisting of:

(i) a treatment step comprising at least one step selected from the group consisting of shredding, drying and pulverizing;
(ii) an extraction step using an extracting solvent; and
(iii) an oozing step,
whereby obtaining at least one member selected from the group consisting of a treated plant, an extract of the plant and an ooze of the plant, each containing an insecticidal component.

The present invention further includes a method for exterminating or controlling injurious insects using the above insecticide.

In the specification, the term "ooze" or "exudate" refers not only to oozes collected from the trunk of a plant but broadly to substances oozed from plants. Moreover, the word "insecticidal" or "insect-repellent" is taken to mean both insecticidability and repellency against insects including injurious insects.

As will be described below, since the insecticide of the present invention comprises an insecticidal component or ingredient derived from a plant specified above, it is highly safe and capable of exterminating and repelling insects (e.g., injurious insects) without adversely affecting the ecosystem of nature.

DETAILED DESCRIPTION OF THE INVENTION

Examples of the plants that belong to the genus Geranium are *Geranium thunbergii* and *Geranium robentianum*. *Geranium thunbergii* is a perennial plant that grows naturally in mountains and fields of all over the country of Japan and is in frequent use as an antidiarrheal agent or a drug for controlling intestinal function. *Geranium robentianum* has been employed as a folk medicine in Europe.

As a plant which belongs to the genus Morus, there may be exemplified *Morus alba* and *Morus bombycis*. *Morus alba* and *Morus bombycis* are deciduous trees naturally growing or cultivated in mountains and field all over the country of Japan, and known for antiinflammatory, diuretic, antitussive, and expectorant components contained therein.

Examples of a plant which belongs to the genus Artemisia, there may be mentioned, e.g., *Artemisia princeps, Artemisia absinthium, Artemisia montana, Artemisia cina, Artemisia capillaris, Artemisia annua, Artemisia scoparia,* and *Artemisia maritima*. *Artemisia princeps* is a perennial (a perennial herb) naturally and wildly growing in mountains and fields of Japan. The dried leave thereof, gaiyo, are decocted and used for relieving stomachache or bellyache and are known to contain antidiarrheal and hemostatic components.

As a plant of the genus Diospyros, there may be exemplified *Diospyros kaki* and *Diospyros ebenum,* and a *kaki* calyx (the dried calyx of an unripe fruit of *Diospyros kaki*) has been employed for getting rid of hiccups.

Examples of a plant of the genus Crataegus are *Crataegus cuneata, Crataegus pentagyna, Crataegus pinnatifida,* and *Crataegus oxyacantha*. They are deciduous shrubs originally from China and found to have stomachic, digestive and intestine function-conditioning effects, antimicrobial activity, and a vasodilating effect, being employed and known also as a cardiotonic agent.

As a plant which belongs to the genus Curcuma, there may be exemplified *Curcuma longa* (domestica), *Curcuma xanthorriza, Curcuma aromatica,* and *Curcuma zedoaria*. *Curcuma longa* (domestics) is a perennial (a perennial herb) originally from tropic Asia and cultivated typically in India and China for medicinal use. It has been known that they contain cholagogic and stomachic components. Also *Curcuma xanthorriza* and *Curcuma aromatica* have been employed as cholagogues or aromatic stomachics.

Examples of a plant of the genus Rubia are *Rubia cordiflolia* var. *munjista* and *Rubia tinctorum*. *Rubia cordiflolia* var. *munjista* is a perennial (a perennial liana) naturally growing in mountains and fields, traditionally having been used as a scarlet dye. In addition, it is known that it contains hemostatic and diuretic components, etc. *Rubia tinctorum* also has been used for dyeing and medical treatment for kidney and diseases of urinary organ, bladder and so forth.

As a plant which belongs to the genus Polygonum, there may be mentioned, for example, *Polygonum tinctorium, Polygonum multiflorum,* and *Polygonum avicurare*. *Polygonum tinctorium* is a plant originally from Indo-China and known as a dye for indigo dyeing. *Polygonum multiflorum* is a perennial plant originally from China and has been used as, e.g., a laxative and a restorative.

Examples of a plant of the genus Gardenia includes *Gardenia jasminoides.*

As a plant which belongs to the genus Cornus, there may be mentioned, e.g., *Cornus officinalis* and *Cornus florida*. *Cornus officinalis* is a deciduous tree (low-height tree) and known for its nutritious components and hemostatic components, etc. It has been known that *Cornus florida* has various physiological effects such as astringency and cordialness.

Examples of a plant of the genus Uncaria include catechu (e.g., *Uncaria gambir*). The catechu is widely distributed over India and mainly cultivated in Malay and Sumatra. The catechu is known to contain components or principles showing astringent and antidiarrheic activity.

As a plant of the genus Rheum, there may be exemplified rhubarbs such as *Rheum palmatum, Rheum coreanum, Rheum officinale,* and *Rheum tanguticum*. The rhubarb (e.g., *Rheum palmatum, Rheum coreanum, Rheum officinale,* and *Rheum tanguticum*) is a plant originally from the Eastern Asia and known to contain active ingredients effective for Taxation, strengthening a weak stomach, controlling intestinal function, etc.

Examples of a plant of the genus Terminalia include *Terminalia chebula* (myrobalan) and *Teminalia bellerica*. The myrobalan is a dried ripen acorn of *Terminalia chebula* which is a deciduous tree originally from India/Myanmar, known to have astringent and antidiarrheal, antitussive, and hemostatic activity.

As a plant which belongs to the genus Saussurea, there may be mentioned, for example, *Saussurea lappa* (saussurea root, costus root). The saussurea root is a dried root of *Saussurea lappa* which is a macroperennial naturally growing in the north of India, and the saussurea root is used as an aromatic stomachic working on diarrhea, vomiting, stomachache, loss of appetite, etc., also known as a perfume.

The aforementioned plants are easily available from where they grow or from the market.

Among the aforementioend plants, those species listed below are preferable for the present invention.

(1a) *Geranium thunbergii* and *Geranium robentianum,*

(2a) *Morus alba* and *Morus bombycis,*

(3a) *Crataegus cuneata, Crataegus pentagyna, Crataegus pinnatifida,* and *Crataegus oxyacantha,*

(4a) *Rubia cordiflolia* var. *munjista* and *Rubia tinctorum,*

(5a) *Artemisia princeps, Artemisia absinthium, Artemisia montana, Artemisia cina, Artemisia capillaris, Artemisia annua, Artemisia scoparia,* and *Artemisia maritima,*

(6a) *Curcuma longa* (domestica), *Curcuma xanthorriza, Curcuma aromatica,* and *Curcuma zedoaria,*

(7a) *Gardenia jasminoides* var. *grandiflora, Gardenia jasminoide,* and *Gardeniae fructus,*

(8a) *Cornus officinalis* and *Cornus florida,*

(9a) *Terminalia chebula* and *Terminalia bellerica,*

(10a) *Saussurea lappa,*

(11a) *Uncaria gambir,*

(12a) *Rheum palmatum, Rheum coreanum, Rheum officinale,* and *Rheum tanguticum,*

(13a) *Diospyros kaki* and *Diospyros ebenum,* and (14a) *Polygonum tinctorium, Polygonum multiflorum,* and *Polygonum avicurare.*

The insecticide or insect-repellent agent of the present invention need only contain insecticidal or insect-repellent ingredients derived from a plant as specified above and may be a processed plant (no extraction) which is, if needed, shredded (or cut), dried, and pulverized (crushed, milled, ground, etc.). The above extract can be obtained according to a conventional method, for example, by processing or treating the plant in such a manner as explained above, then extracting the processed plant (or the treated plant) with a suitable solvent under atmospheric pressure or applied pressure and at room temperatures or on heating. Thereafter, the resultant extract is filtered and condensed, if needed. The plant can be subjected to extraction either singly or in combination.

The part (organ) of the plant to be subjected to extraction is different depending on the species and may be the whole or a part (organ), such as root, stem (stalk), leaf, fruit or acorn (nut), seed, rind (pericarp), cortex (bark), trunk, branch, and flower. For example, a whole plant body of (1) the genus Geranium can be subjected to extraction. A part(s) (organ) of a plant of each genus to be subjected to extraction is as listed below.

The genus Morus (2): root bark

The genus Artemisia (5) and the genus Polygonum (14): leave

The genus Diospyrous (13): calyx

The genus Crataegus (3), the genus Gardenia (7), the genus Cornus (8) and the genus Terminalia (9): usually, fruits or acorns thereof The genus Curcuma (6), the genus Rubia (4), the genus Rheum (12) and the genus Saussaurea (10): root stock (including main root stock)

Further, use can be made of the catechu of the genus Uncaria (11) commercially available in the form of an extract.

As the extracting solvent, there may be exemplified water; alcohols such as methanol, ethanol, n-propanol, i-propanol, n-butanol, i-butanol, sec-butanol, t-butanol, n-octanol, and cyclohexanol; ethers such as ethyl ether, propyl ether, isopropyl ether, dimethoxyethane, cyclic ethers (e.g., dioxane, tetrahydrofuran), mono- or di-alkylene glycol monoalkylethers (e.g., ethylene glycol monomethylether, ethylene glycol monoethylether, diethylene glycol monoethylether); ketones such as acetone, methyl ethyl ketone, methyl isobutyl ketone, and cyclohexanone; esters such as ethyl acetate and butyl acetate; halogenated hydrocarbons such as carbon tetrachloride, chloroform, dichloromethane and 1,2-dichloroethane; aliphatic hydrocarbons such as hexane and octane; alicyclic hydrocarbons such as cyclohexane and cycloheptane; aromatic hydrocarbons such as benzene, toluene and xylene; nitrites such as acetonitrile; carboxylic acids such as formic acid and acetic acid; and aprotic polar solvents such as N,N-dimethylformamide, dimethyl sulfoxide, and pyridine. These solvents can be used either singly or in combination.

Of these solvents, preferred extracting solvents include water, hydrophilic solvents, and mixtures thereof. The preferred hydrophilic solvents include, e.g., straight- or branched chain alcohols having about 1 to 4 carbon atoms; ethers such as dimethoxyethane, cyclic ethers, mono- or di-alkylene glycol monoalkylethers; ketones such as acetone; nitriles; organic carboxylic acids; and aprotic solvents.

Particularly preferred solvents include water; water-soluble (or water-miscible) solvents such as straight- or branched alcohols having 1 to 4 carbon atoms, and acetone; and mixtures thereof.

The amount of the extracting solvent need only be in the range not adversely affecting the extractability or extracting operations. For example, the amount of the solvent is about 50 to 10,000 parts by weight, preferably about 70 to 5,000 parts by weight, and more preferably about 100 to 2,000 parts by weight, relative to 100 parts by weight of the plant to be extracted from. The extraction temperature is, e.g., about 0 to 150° C. and preferably in the range of from room temperatures (e.g., 25° C.) to about 120° C.

The ooze (or exudate) used in the present invention can also be obtained in a conventional manner. For example, a part (organ) of a plant body, e.g., the trunk of a tree, is cut or scratched to collect an ooze (or exudate) such as a resinous substance, or the whole plant body or a part (organ) thereof is treated (or heat-treated) with hot water if necessary and then squeezed or pressed, and the ooze or exudate thereof is collected. In the present invention, not only the ooze or exudate isolated from the plant in such manner but also an ooze or exudate naturally oozed from the plant body or a part thereof can be used. For example, in some substances, from a processed plant (crushed or pulvelized, dried, etc.) may be oozed some substances as exudates. The term "ooze (or exudate)" used in the specification includes such oozed substances or exudates.

In the present invention, a plurality of plants, extracts, or oozes, of different genera may be mixed together. Moreover, a combination of two or more members selected from the group consisting of a processed plant, an extract, and an ooze (or exudate) may also be used. The extract and ooze may be in liquid form, or in solid form as a powder or particulates, or in semi-solid form as a paste. The processed plant, extract, and ooze (exudate) contain insecticidal or insect-repellent components highly effective against insects (e.g., injurious insects). In addition to that, these insecticidal or insect-repellent components are natural ones and derived from edible plants or plants for crude drug, being usually safe to human beings and animals and less harmful to the environment.

In the insecticide or insect-repellent agent of the present invention, there is no specific limitation in its form so far as it contains the above ingredient or component, and it may be the plant processed or its extract or ooze (exudate) itself. Moreover, the insecticide or insect-repellent agent may be in the form of a preparation. Examples of the form of the preparation include liquids such as solution, water-containing agent, dispersion, suspension, emulsion, oil, and lotion; solids such as powder, granules, microcapsules, microspheres, flowable agent, and foaming agent; semi-solids such as pastes and creams; atomizing agent, aerosol; and coating composition. These can suitably be selected according to the intended use and where to be applied to. These preparations can be produced in accordance with conventional processes.

The above liquid or semi-solid preparation can be produced by, for example, diluting the above extract or ooze (exudate) with a suitable liquid diluent or a carrier. In the case of a water-containing agent, a solid diluent or carrier may be further incorporated thereto.

As the liquid diluent or carrier, there may be exemplified, in addition to the extracting solvents exemplified above, alcohols such as ethylene glycol, propylene glycol, and glycerol; plasticizers (e.g., ester-series plasticizers such as di-2-ethylhexyl adipate); petroleum-series solvent such as kerosene; aromatic hydrocarbons such as ethylnaphthalene and phenylxylylethane; and phosphates such as 2-ethylhexyl phenyl phosphate. The liquid diluent or carrier can be used either singly or in combination. As the solid diluent or carrier, use can be made of diatomaceous earth, mica, clay, kaolin, talc, powdered quartz, bentonite, and the like. These solid diluents or carriers are also can be used either singly or as a mixture thereof.

The solid preparation can be produced by, for example, diluting or granulating (or pelletizing) the extract or ooze with a suitable solid diluent or carrier. As the solid diluent or carrier, there may be exemplified, besides the solid diluents exemplified above, talc such as powdered talc and powdered agalmatolite, clay such as finely powdered clay, mineral powders such as calcium carbonate, etc.; sulfur powder; urea powder; vegetable powders such as wood flour and starch; and various carriers frequently used for agrochemical compositions and horticultural preparations, etc. These solid diluents or carriers are often used as extenders and can be used either singly or in combination.

The aerosol can be produced by diluting the extract or ooze (exudate) with a suitable solvent if needed and charging a container or vessel with the diluted extract or ooze together with a propellant. As the solvent, there may be mentioned those exemplified above. As the propellant, there may be mentioned, for example, flon and liquefied natural gas.

If needed, to the insect-repellent agent or insecticide may be added various additives according to the type of the preparation. Examples of the additive are antiseptic/ antimold agents; stabilizers such as antioxidants and ultraviolet ray absorbents; binders; film-formable resins; emulsifying agents, dispersants, spreading agents, wetting agents; penetrants; thickeners; auxiliary fluidizing agents; consolidation inhibiting agents; flocculating agents; ultraviolet ray scattering agents; dehydrating agents, and colorants.

As an example of the above antiseptic/antimold agent, there may be exemplified iodine-containing organic compounds such as 3-bromo-2,3-diiodo-2-propenyl ethyl carbonate, 3-iodo-2-propynyl butyl carbamate, 2,3,3-triiodo allyl alcohol, and parachlorophenyl-3-iodopropargylformal; benzimidazole compounds and benzthiazole compounds such as 2-(4-thiazolyl)benzimidazole and 2-thiocyanomethylthiobenzo-thiazole; triazole compounds such as 1-(2-(2',4'-dichlorophenyl)-1,3-dioxolane-2-ylmethyl)-1H-1,2,4-triazole, 1-(2-(2',4'-dichlorophenyl)-4-propyl-1,3-dioxolane-2-ylmethyl)-1H-1,2,4-triazole, and α-(2-(4-chlorophenyl)ethyl)-α-(1,1-dimethylethyl)-1H-1,2,4-triazole-1-ethanol; and naturally occurring compounds such as 4-isopropyltropolone(hinokitiol) and borax.

As an antioxidant, there may be exemplified phenolic antioxidants such as 4,4'-thiobis-6-t-butyl-3-methylphenol, butylated hydroxyanisole (a mixture of 2-t-butyl-4-methoxyphenol and 3-t-butyl-4-methoxyphenol), p-octylphenol, mono (or di- or tri-)-(α-methylbenzyl) phenol, 2,6-di-t-butyl-p-cresol (BHT), and pentaerythrityl tetrakis[3-(3,5,-di-t-butyl-4-hydroxyphenyl)]propionate; amine antioxidants such as N,N'-di-2-naphthyl-p-phenylenediamine; hydroquinoline antioxidants such as 2,5-di(t-amyl)hydroquinoline; sulfur-containing antioxidants such as dilauryl thiodipropionate; and phosphorus-containing antioxidants such as triphenyl phosphite.

As a ultraviolet ray absorbent, there may be mentioned, for example, benzotriazole compounds such as 2-(2'-hydroxy-5'-methylphenyl)benzotriazole and 2-(2'-hydroxy-4'-n-octoxyphenyl)benzotriazole; benzophenone compounds such as 2-hydroxy-4-methoxybenzophenone and 2-hydroxy-4-n-octoxybenzophenone; salicylic acid compounds such as phenyl salicylate and p-t-butylphenyl salicylate; 2-ethylhexyl 2-cyano-3,3-diphenyl acrylate, 2-ethoxy-2'-ethyl oxalic bisanilide, and dimethyl succinate-1-(2-hydroxyethyl)-4-hydroxy-2,2,6,6-tetramethylpiperidine polycondensate.

As a binder, there may be exemplified a sodium salt of carboxymethylcellulose, methyl cellulose, ethyl cellulose, hydroxymethyl cellulose, dextrin, α-starch, polyvinyl alcohol, polyvinylpyrrolidone, sodium ligninsulfonate, and potassium ligninsulfonate.

Examples of the film-formable resin are thermoplastic resins (e.g., polyolefinic resins such as polyethylene and polypropylene, polyvinyl acetate, polyvinyl alcohol, acrylic resins, polyvinyl chloride, styrenic resins, fluororesins, chlorinated polyolefins, alkyd resins, polyamide, and polyester); and thermosetting resins such as phenolic resins, urea resins, melamine resins, furan resins, unsaturated polyester resins, and epoxy resins.

As an emulsifying agent, a dispersant, a spreading agent, a wetting agent, or a penetrant, conventional surfactants such as anionic surfactants and nonionic surfactants can be employed. Examples of the anionic surfactant are metallic soaps, salts of sulfuric esters such as sodium alkylsulfate, alkylbenzene sulfonates such as sodium alkylbenzene sulfonate, alkylnaphthalenesulfonates such as sodium alkylnaphthalene sulfonate [e.g., NewCalgen BX-C (tradename), manufactured by Takemoto Yushi, K.K.), salts of dialkyl 2-sulfosuccinates such as sodium dialkyl 2-sulfosuccinate [e.g., Neocol SW-C (tradename), manufactured by Dai-ichi Kogyo Seiyaku Co., Ltd.], polycarboxylic acid-based surfactants [e.g., Toxanon GR-30 (tradename), manufactured by Sanyo Kasei Co., Ltd.], α-olefin sulfonates, polyoxyethylenedistyrenephenylether sulfate ammonium salt [e.g., Dixzol 60A (tradename), manufactured by Dai-ichi Kogyo Seiyaku Co., Ltd.], sodium ligninsulfonate, and potassium ligninsulfonate. Examples of the nonionic surfactant are polyoxyethylene alkyl ethers and polyoxyethylenealkylarylether [e.g., Noigen EA-142 (tradename), manufactured by Dai-ichi Kogyo Seiyaku Co., Ltd. (EA-142)], polyoxyethylenearylether, esters of fatty acids with polyhydric alcohols, fatty acid polyhydric alcohol polyoxyethylenes, fatty acid esters of sucrose, block copolymers of ethylene oxide and propylene oxide [e.g., Newpol PE-64 (tradename), manufactured by Sanyo Kasei Co., Ltd.].

As a thickener, there may be mentioned, e.g., polyvinyl alcohol, polyacrylic acid and salts thereof. Examples of an auxiliary fluidizing agent are organic lubricants such as PAP subsidiary agents (e.g., isopropylphosphoric acid), wax, polyethylene, metal salts of fatty acids, paraffin, and silicone oils, and inorganic lubricants such as talc. As a consolidation inhibitor (or an anti-blocking agent), there may be mentioned, for example, white carbon, diatomaceous earth, magnesium stearate, aluminum oxide, and titanium dioxide. Examples of a flocculating agents are liquid paraffin, ethylene glycol, diethylene glycol, triethylene glycol, and isobutylene polymers [e.g., produced by Idemitsu Petroleum Chemicals Co., Ltd., IP solvent-2835 (tradename)]. As the ultraviolet ray scattering agent, use can be made of, for example, titanium dioxide. Examples of a dehydrating agent are drying agents such as anhydrous gypsum and silica gel powder. Examples of a colorant include organic and inorganic pigments and dyes.

The insecticide or insect-repellent agent of the present invention may contain other insecticide or insect-repellent agent, or an effect enhancing agent. Other insecticides include organophosphorus insecticides such as Phoxim, Chlorpyrifos, fenitrothion, pyridaphenthion, isofenphos; carbamate-series compounds such as Bassa and Propoxur; pyrethroid insecticides such as Cyfluthrin, Permethrin, Tralomethrin, phenvalerate, Ethofenprox, and Hoe-498; neonicotinoid insecticides such as imidacloprid, nitenepyram, and acetamiprid, phenylpyrazole insecticides such as fipronil, nereistoxin compounds such as bensultap, hiba oil, hiba neutral oil, fatty acids such as decanoic acid and octanoic acid, boric acids, and plants such as the neem tree [Japanese Patent Application Laid-Open No. 41011/1991 (JP-A-3-41011)], and those belong to the genus Moringa and the genus Marah [Japanese Patent Application Laid-open No. 329514/1994 (JP-A-6-329514). Moreover, the insecticide of the present invention may contain a chitin synthesis inhibiting agent or inhibitor such as lufenuron, hexaflumuron, diflubenzuron and flufenoxuron or a juvenile hormone analogues such as methoprene and hydroprene, known as an insect growth regulator (IGR).

The content of the insecticidal or insect-repellent component can suitably be selected according to the form of the preparation or its application manner and is usually 0.01 to 80% by weight. When the preparation is in liquid form, or semi-solid or solid form, the concentration of the ingredient contained in the insecticide in terms of the extract or ooze (exudate) of the plant is, for example, about 0.1 to 80% by weight and preferably about 0.5 to 50% by weight. When the agent is in aerosol form, the concentration of the ingredient in the charge filling a container is, in terms of the extract or exudate of the plant, for example about 0.01 to 25% by weight and preferably about 0.05 to 15% by weight.

The insecticide or insect-repellent agent of the present invention is applicable to various insects [e.g., injurious insects such as hygienically injurious ones (e.g., cockroaches, flies, mosquitoes, horseflies, bedbugs) and insects injurious to timber (e.g., termites, for example, (1) insects which belong to Isoptera, for example, those belonging to Rhinotemitidae such as *Reticulitormes speratus* and *Coptotermes formosanus*, and those belonging to Kalotermitidae such as *Cryptotermes domesticus*, and (2) insects which belongs to Coleoptera, for example, those belonging to Lyctidae such as *Lyctus brunneus, Lyctus linearis, Lyctus sineusis,* and *Lyctoxylon dentatum*). Even with a small dose of the insecticide or insect-repellent agent of the present invention exhibits efficient insecticidal activity when used to exterminate or control insects (e.g., insects injurious to houses such as termites) The insecticide of the present invention is effective especially to termites. Any one of the insecticidal or insect-repellent components or ingredients derived from the plants of the above-mentioned genera (1) to (14) is capable of exterminating or controlling termites effectively. Insecticidal or insect-repellent components or ingredients derived from the plants of the species (1a) to (14a) are effective and useful for exterminating or controlling termites. Such effects can be obtained even when a plant body itself is employed.

In the method of the present invention for exterminating and controlling insects (for example, injurious insects), the above insecticide is directly applied to insects, or indirectly acts on insects by being applied to spots or pathways along which insects come in or where they infest (or breed, or swarm), for example, kitchen, bath room, living room, the corners of the floor, under the floor, in the ceiling, the foundation of a house, pillars, walls, and the ground. The insecticide is applied in a manner suitable for an invasion or infestation spot (or invasion pathway, etc.) of insects (e.g., injurious insects), and various ways of application can be mentioned, such as coating, distributing, dipping or impregnating, injecting, mixing, and atomizing. When applying the insecticide to the soil or ground, the insecticide is distributed over the surface of the ground or along the grooves formed in the ground, or mixed with the soil. Further, the insecticide can exhibit its insect-repellent or insecticidal activity even when disposed on or applied to the above-mentioned invasion or breeding spots in the form of a sheet-type agent formed by allowing a sheet-like base material (substrate) such as a synthetic resin sheet, paper, or fabrics to support the insecticide by means of coating, impregnation, or kneading.

In the method of the present invention, the above-described insect-repellent or insecticidal ingredient exterminates or repels insects such as injurious insects (particularly, termites) efficiently and thus remarkably reduces the damage caused by such insects. Moreover, the application of the insecticide of the present invention to timber enables the preservation of timber without damage by insects such as termites.

The present insecticide can be applied to timber by various ways such as coating, dipping, impregnating, submerging, and injecting.

Among the genera listed above in the present invention, those genera (1) the genus Geranium, (2) the genus Morus, (3) the genus Crataegus, and (4) the genus Rubia are preferable.

Especially, an insecticide comprising a component or ingredient derived from a plant of the genus (1), (2), (3), (4), (5) the genus Artemisia or (6) the genus Curcuma is useful for preserving timber.

In the present invention, an insecticide comprising a plant which belongs to at least one genus selected from the group consisting of (5) the genus Artemisia and (6) the genus Curcuma, being applicable to insects injurious to timber, is preferable.

Furthermore, in the present invention, an insecticide comprising a plant which belongs to at least one genus selected from the group consisting of (11) the genus Uncaria, (12) the genus Rheum, (13) the genus Diospyros and (14) the genus Polygonum, being applicable to termites, is preferable.

Moreover, in the present invention, an insecticide comprising a plant which belongs to at least one species selected from the group consisting of *Artemisia princeps, Artemisia montana, Artemisia cina, Artemisia capillaris, Artemisia annua, Artemisia absinthium, Artemisia scoparia, Artemisia maritima, Curcuma longa, Curcuma xanthorriza, Curcuma aromatica, Curcuma zedoaria, Rheum palmatum, Rheum coreanum, Rheum officinale,* and *Rheum tanguticum*, being applicable to termites, is preferable.

The insecticide of the present invention exhibits excellent insecticidal or insect-controlling effect against insects (e.g., injurious insects). Moreover, since the insect-repellent and insecticidal ingredient or component is derived from a natural plant, the insecticide of the present invention is highly safe to human beings and animals and less harmful to the environment.

According to the production process of the present invention, such an excellent insecticide having characteristics as described above can be obtained with such a simple and easy operation as extraction or exudation.

According to the method of the present invention for exterminating and controlling insects (e.g., injurious insects), and insects (e.g., injurious insects) are repelled or exterminated with efficiency and safety.

EXAMPLES

Hereinafter, the present invention will be described in further detail but should by no means be construed as defining the scope of the invention.

Example 1

To 6 g of a dry, powdered whole plant body of *Geranium thunbergii* of the genus Geranium was added 60 g of methyl alcohol and extraction was conducted for 30 minutes using ultrasonic wave. Thereafter, the resultant extract was filtrated and condensed. To the resultant condensate was added methyl alcohol so that the concentration of the condensed extract is 10% by weight relative to methyl alcohol, and there was obtained a sample solution containing the extract. The yield of the extract from the plant was 16.7%.

Example 2

Except that the root bark of the mulberry tree of the genus Morus was used, the same operations as in Example 1 were performed. The yield of the extract from the plant was 12.1%.

Example 3

Except that the gaiyo of a plant of the genus Artemisia (dried leave of *Artemisia princeps*) was used, the same operations as in Example 1 were performed. The yield of the extract from the plant was 10.0%.

Example 4

Except that the calyx of a plant of the genus Diospyros (the calyx of *Diospyros kaki*), the same operations as in Example 1 were performed. The yield of the extract from the plant was 22.1%.

Example 5

Except that the fruits of *Crataegus cuneata* of the genus Crataegus were used, the same operations as in Example 1 were performed. The yield of the extract from the plant was 25.8%.

Example 6

Except that the main root stock of *Curcuma (longa) domestica* of the genus Curcuma (from India) was used, the same operations as in Example 1 were performed. The yield of the extract from the plant was 19.1%.

Example 7

Except that the main root stock of *Curcuma longa* (domestics) of the genus Curcuma (from China) was used, the same operations as in Example 1 were performed. The yield of the extract from the plant was 7.2%.

Example 8

Except that the root of *Rubia cordiflolia* var. *munjista* of the genus Rubia was used, the same operations as in Example 1 were performed. The yield of the extract from the plant was 5.8%.

Example 9

Except that the leave of *Polygonum tinctorium* of the genus Polygonum were used, the same operations as in Example 1 were performed. The yield of the extract from the plant was 19.4%.

Example 10

Except that the fruit of *Gardeniae fructus* of the genus Gardenia was used, the same operations as in Example 1 were performed. The yield of the extract from the plant was 23.6%.

Example 11

Except that the fruit of *Cornus officinalis* of the genus Cornus, the same operations as in Example 1 were performed. The yield of the extract from the plant was 47.3%.

Example 12

The extract of the catechu of the genus Uncaria which is commercially available was used.

Example 13

Except that the rhizome of the rhubarb of the genus Rheum was used, the same operations as in Example 1 were performed. The yield of the extract from the plant was 37.3%.

Example 14

Except that the acorn of *Terminalia chebula* of the genus Terminalia was used, the same operations as in Example 1 were performed. The yield of the extract from the plant was 47.1%.

Example 15

Except that the root of *Saussurea lappa* of the genus Saussurea was used, the same operations as in Example 1 was performed. The yield of the extract from the plant was 45.0%.

Example 16

Except that the main root stock of *Curcuma zedoaria* of the genus Curcuma was used, the same operations as in Example 1 was performed. The yield of the extract from the plant was 7.0%.

Experiment 1

Quartz sand passed through a sieve of 20 mesh was dried at 60° C.±2° C. until a constant weight was reached and then cooled to give quartz sand for test. Thereafter, the sample solution was uniformly applied on the surfaces of the grains of the quartz sand (12 g) in an amount such that the amount of the extract relative to the quartz sand was 1% by weight, and the solvent (methanol) was evaporated off. Further, the quartz sand was moistened to have the water content of 10% by weight relative to the dried quartz sand. For comparison, moistened quartz sand without being treated with the sample solution was prepared in the same manner as the control.

Two cylindrical glass vessels each having the bottom and a joining or coupling part protruded 2 cm from one end of the vessel (inside diameter: 5 cm, height: about 12 cm) and a glass tube (inside diameter: 1.5 cm, length: about 10 cm) for joining or coupling the two glass vessels were employed. The glass vessels and the glass tube had been dry-sterilized. One of the glass vessels was fed with about 60 g of the agent-free or untreated quartz sand for test, and the other glass vessel was fed with about 3 g of Japanese red pine chips. The central part of the glass tube was filled with the quartz sand treated with the sample solution or the untreated quartz sand, and the two glass vessels were joined together with this glass tube. Two hundred ergates and twenty dinergates of *Coptotermes formosanus* collected from their nest were put into the glass vessel filled with the untreated quartz sand for test, and the testing apparatus was allowed to stand in a thermostated chamber kept at a temperature of 28±2° C. and at a humidity of 70% or higher for three weeks.

After three weeks, whether the *Coptotermes formosanus* put into the glass vessel fed with the quartz sand for test had moved to the other glass vessel filled with Japanese red pine chips through the glass tube or not was observed. These procedures were repeated three times for each sample.

The results are shown in Table 1. In the table, the degree of the depth of the hole made in the quartz sand treated with the sample solution by the termite when it moved to the other glass vessel filled with Japanese red pine chips was evaluated and graded according to the following standards.

A . . . Excellent
B . . . Good
C . . . Failure

If the depth is less than 1 cm (A and B), the insecticidal or insect-repellent effect against *Coptotermes formosanus* can be considered to be satisfactory.

TABLE 1

|  | After 2 hours | After 4 hours | After 6 hours | After 1 day | After 2 days | After 3 days | After 4 days | After 7 days |
|---|---|---|---|---|---|---|---|---|
| Example 1 | A | A | A | A | A | A | A | A |
| Example 2 | A | A | A | A | A | A | A | A |
| Example 3 | A | A | A | A | A | A | A | A |
| Example 4 | A | A | A | A | A | A | A | A |
| Example 5 | A | A | A | A | A | A | A | A |
| Example 6 | A | A | A | A | A | A | A | A |
| Example 7 | A | A | A | A | A | A | A | A |
| Example 8 | A | A | A | A | A | A | A | A |
| Example 9 | A | A | A | A | A | A | A | A |
| Example 10 | A | A | A | A | A | A | A | A |
| Example 11 | B | B | B | B | B | B | B | B |
| Example 12 | B | | | | | | | C |
| Example 13 | B | B | B | B | B | B | B | B |
| Example 14 | B | B | B | B | B | B | B | B |
| Example 15 | B | B | B | B | B | B | B | B |
| Example 16 | A | A | A | A | A | A | | |
| Comp. Ex. | C | C | C | C | C | C | C | C |

The depth of the hole made by the movement of the termite
A (excellent): no penetration was observed in the quartz sand
B (good): partly dug (less than 1 cm)
C (failure): dug throughout the quartz sand [Exmaple 12 (catechu) 4 cm, Comparative Example (control) 5 cm]

As shown in Table 1, the depth of the hole made in the quartz sand treated with the sample solution in each experiment of Examples 1 to 16 is 4 cm in Example 12 (catechu), and less than 1 cm in Example 11 (*Cornus officinalis*), Example 13 (rhubarb), Example 14 (*Terminalia chebula*) and Example 15 (*Saussurea lappa*), but no movement of the termite was observed in the rest of the examples. Contrary to these results, in the case where the glass tube was filled with the untreated quartz sand (comparative example), the termites moved through the glass tube filled with the quartz sand, penetrated the sand (about 5 cm depth), and reached the glass filled with Japanese red pine chips. As can be understood from these results, the quartz sand treated with the sample solution in Examples 1 to 16 were recognized to have a high insect-repellent effect against *Coptotermes formosanus*.

Experiment 2

Quartz sand treated in a similar manner as in the experiment 1 and the untreated quartz sand were independently laid in the petri dishes (diameter: 6 cm) dry-sterilized. Ten ergates of *Coptotermes formosanus* collected from their nest were put on the quartz sand randomly. Thereafter, each petri dish was put into a container with water in it and the container was left in a chamber thermostated at a temperature of 28° C. ±2° C. for 1 week. The health condition of the termites was observed after one day and after one week. For comparison, in the comparative example, the quartz sand which is not treated with the sample solution (control) was used.

The results are shown in Table 2. In the Table, the numbers filling the items (a), (b), and (c) represent the number of healthy termites, the number of knocked-down termites, and the number of dead termites, respectively.

TABLE 2

| | After 2 hours | | | After 4 hours | | | After 6 hours | | | After 1 day | | | After 2 days | | | After 3 days | | | After 4 days | | | After 7 days | | |
|---|---|---|---|---|---|---|---|---|---|---|---|---|---|---|---|---|---|---|---|---|---|---|---|---|
| | a | b | c | a | b | c | a | b | c | a | b | c | a | b | c | a | b | c | a | b | c | a | b | c |
| Ex. 1 | 0 | 2 | 8 | 0 | 0 | 10 | | | | | | | | | | | | | | | | | | |
| Ex. 2 | 0 | 3 | 7 | 0 | 0 | 10 | | | | | | | | | | | | | | | | | | |
| Ex. 3 | 0 | 5 | 5 | 0 | 0 | 10 | | | | | | | | | | | | | | | | | | |
| Ex. 4 | 3 | 4 | 3 | 0 | 5 | 5 | 0 | 0 | 10 | | | | | | | | | | | | | | | |
| Ex. 5 | 9 | 1 | 0 | 3 | 7 | 0 | 0 | 4 | 6 | | | | 0 | 0 | 10 | | | | | | | | | |
| Ex. 6 | 10 | 0 | 0 | | | | 8 | 2 | 0 | 0 | 1 | 9 | 0 | 0 | 10 | | | | | | | | | |
| Ex. 7 | 10 | 0 | 0 | 9 | 1 | 0 | 2 | 8 | 0 | 0 | 1 | 9 | 0 | 0 | 10 | | | | | | | | | |
| Ex. 8 | 10 | 0 | 0 | | | | 7 | 3 | 0 | 3 | 3 | 4 | 0 | 0 | 10 | | | | | | | | | |
| Ex. 9 | 9 | 1 | 0 | 8 | 2 | 0 | 5 | 3 | 2 | 0 | 4 | 6 | 0 | 0 | 10 | | | | | | | | | |
| Ex. 10 | 10 | 0 | 0 | | | | | | | | | | 9 | 1 | 0 | | | | 5 | 0 | 5 | 0 | 0 | 10 |
| Ex. 11 | 9 | 1 | 0 | 9 | 0 | 1 | | | | 8 | 0 | 2 | | | | | | | | | | 0 | 0 | 10 |
| Ex. 12 | 10 | 0 | 0 | | | | | | | | | | | | | | | | | | | 0 | 0 | 10 |
| Ex. 13 | 10 | 0 | 0 | 10 | 0 | 0 | 10 | 0 | 0 | 10 | 0 | 0 | 10 | 0 | 0 | 10 | 0 | 0 | 10 | 0 | 0 | 10 | 0 | 0 |
| Ex. 14 | 10 | 0 | 0 | | | | | | | | | | 0 | 4 | 6 | 0 | 0 | 10 | | | | | | |
| Ex. 15 | 10 | 0 | 0 | 10 | 10 | 0 | 10 | 0 | 0 | 10 | 0 | 0 | 10 | 0 | 0 | 10 | 0 | 0 | 10 | 0 | 0 | 10 | 0 | 0 |
| Ex. 16 | 10 | 0 | 0 | 10 | 0 | 0 | 8 | 2 | 0 | 6 | 3 | 1 | 0 | 5 | 5 | 0 | 0 | 10 | | | | | | |
| Comp. Ex. | 10 | 0 | 0 | 10 | 10 | 0 | 10 | 0 | 0 | 10 | 0 | 0 | 10 | 0 | 0 | 10 | 0 | 0 | 10 | 0 | 0 | 10 | 0 | 0 |

The health condition of the termite (a: healthy b: knocked-down c: dead)

As can be understood from the results of the health condition of *Coptotermes formosanus* shown in Table 2, 10 termites were all dead in 4 hours in Examples 1 to 3, 6 hours in Example 4, 2 days in Examples 5 to 9, 3 days in Example 16, 4 days in Example 14, and in 7 days in Examples 10 to 12, indicating the insecticidal activity of the components of these plants. In Examples 13 and 15, no insecticidal effect was observed, but the insecticidal or insect-repellent activity against *Coptotermes formosanus* in the Experiment 1 reached the desired level (the depth of the hole dug in the quartz sand was less than 1 cm). In contrast to the Experiment 1 in which the insecticidal activity was not exhibited to a required degree for Example 12, high insecticidal activity was recognized for Example 12 in the Experiment 2. Therefore, the insecticidal or insect-controlling effect of the present invention can be considered to be valid.

What is claimed is:

1. An insecticide applicable to a termite, comprising at least one member selected from the group consisting of a processed plant, an extract of a plant, and an exudate of a plant, each containing an insecticidal component, wherein said plant belongs to at least one genus or species selected from the group consisting of:
   (1) the species *Geranium thunbergii* or the species *Geranium robentianum*,
   (2) the genus Morus,
   (3) the genus Crataegus,
   (4) the genus Gardenia,
   (5) the species *Cornus officinalis*,
   (6) the genus Terminalia,
   (7) the genus Saussurea,
   (8) the genus Uncaria,
   (9) the genus Rheum,
   (10) the species *Diospyros kaki*,
   (11) the species *Polygonum multiflorum*, and
   (12) the species *Polygonum aviculare*.

2. An insecticide according to claim 1, wherein said plant belongs to at least one genus selected from the group consisting of:
   (1) the species *Geranium thunbergii* or the species *Geranium robentianum*,
   (2) the genus Morus, and
   (3) the genus Crataegus.

3. An insecticide according to claim 1, wherein said plant belongs to at least one genus selected from the group consisting of:
   (9) the genus Uncaria, and
   (10) the genus Rheum.

4. An insecticide according to claim 1, wherein said plant belongs to at least one species selected from the group consisting of:
   *Rheum palmatum*, *Rheum coreanum*, *Rheum officinale*, and *Rheum tanguticum*.

5. An insecticide according to claim 1 wherein said extract is a substance extracted with at least one member selected from the group consisting of water and a hydrophilic solvent.

6. An insecticide according to claim 1, wherein the amount of said insecticidal component is 0.01 to 80% by weight based on the amount of the insecticide in terms of the extract or exudate.

7. An insecticide according to claim 1, wherein said insecticide is in the form of a liquid preparation, a solid preparation, a semi-solid preparation, a spray, an aerosol, or a coating composition.

8. A process for producing an insecticide which comprises subjecting a plant recited in claim 1 to at least one step selected from the group consisting of:
   (i) a treatment step comprising at least one step selected from the group consisting of shredding, drying and pulverizing;
   (ii) an extraction step using an extracting solvent; and
   (iii) an exudating step,
   thereby obtaining at least one member selected from the group consisting of a treated plant, an extract of the plant and an exudate of the plant, each containing an insecticidal component.

9. A process according to claim 8, wherein the extracting solvent is at least one member selected from the group consisting of water, an alcohol, an ether, a ketone, an ester, a halogenated hydrocarbon, an aliphatic hydrocarbon, an alicyclic hydrocarbon, an aromatic hydrocarbon, a nitrile, a carboxylic acid, and an aprotic polar solvent.

10. A process according to claim 8, wherein the extracting solvent is at least one member selected from the group consisting of water and a hydrophilic solvent.

11. A method for exterminating or controlling a termite by exposing the termite to an insecticide recited in claim 1.

12. A method according to claim 11, wherein said insecticide is applied to a termite, or an invasion or infestation spot.

13. A method according to claim 12, wherein said insecticide is applied to the spot by coating, distributing, dipping, impregnating, injecting, mixing, or atomizing.

* * * * *